United States Patent [19]

McKenna, III

[11] 3,959,321

[45] May 25, 1976

[54] STABILIZED FATTY ACIDS

[75] Inventor: Arthur L. McKenna, III, Wheeling, Ill.

[73] Assignee: Kraftco Corporation, Glenview, Ill.

[22] Filed: May 13, 1974

[21] Appl. No.: 469,440

Related U.S. Application Data

[63] Continuation of Ser. No. 346,336, March 30, 1973, abandoned.

[52] U.S. Cl............................... 260/398.5; 260/540
[51] Int. Cl.² ........................................... C11B 5/00
[58] Field of Search........................ 260/398.5, 540

[56] References Cited
UNITED STATES PATENTS

| | | | |
|---|---|---|---|
| 2,926,093 | 2/1960 | Cyba............................... | 260/398.5 |
| 3,812,220 | 5/1974 | Robin et al. ................. | 260/398.5 X |

*Primary Examiner*—Patrick P. Garvin
*Attorney, Agent, or Firm*—Fitch, Even, Tabin & Luedeka

[57] ABSTRACT

Fatty acids are stabilized by adding to the fatty acid an effective amount of an alkali metal salt of particular organic phosphate esters. The stabilizer contains from about 5 to 15 percent phosphorus and from about 10 to about 30 percent alkali metal, with the balance being derived from organic alcohols.

24 Claims, No Drawings

STABILIZED FATTY ACIDS

The present invention is a continuation of U.S. patent application Serial No. 346,336, filed Mar. 30, 1973 now abandoned.

The present invention relates generally to the stabilization of fatty acids to prevent oxidation and decolorization thereof. More particularly, the present invention is directed to the use of particular potassium salts of organic phosphorus compounds to stabilize fatty acids.

As used herein the term "fatty acids" refers to long chain saturated and unsaturated aliphatic, mono-carboxy acids having a carbon chain length of from $C_6$ to $C_{24}$.

The color of fatty acids is important because many fatty acids find extensive use in products like cosmetics, resinous coatings and food, where whiteness or lightness of color is important. It is well known that fatty acids tend to decolorize upon standing. It is believed that the decolorization is due to oxidation of the fatty acids. All fatty acids have some tendency to combine with oxygen to form impurities which are objectionable from the color or odor standpoint. This tendency is lesser for the long chain saturated acids except at elevated temperatures. It is more pronounced with short chain fatty acids and particularly with the unsaturated fatty acids. The reaction is catalyzed by traces of the metal salts of iron or copper. Various antioxidant materials have been used and have been proposed for the purpose of stabilizing fatty acids. However, the proposed antioxidant materials have not proved completely satisfactory and it would be desirable to provide improved stabilizers for fatty acids to prevent decolorization and oxidation of the fatty acids during storage, and particularly during heating of the fatty acids.

Accordingly, it is a principal object of the present invention to provide stabilized fatty acids. It is another object of the present invention to provide particular potassium salts of organic phosphorus compounds which are effective stabilizers for fatty acids. It is a further object of the present invention to provide a method for stabilizing fatty acids against darkening and oxidation, particularly during heating. It is a still further object of the present invention to provide a method for preventing decolorization of fatty acids by adding a potassium salt of organic phosphorus compounds thereto.

These and other objects of the present invention will become more apparent from the following detailed description.

Generally, in accordance with various features of the present invention, fatty acids are stabilized by adding to the fatty acids an effective amount of an alkali metal salt of particular organic phosphate esters. Generally, the stabilizer of the present invention contains from about 5 to about 15 percent phosphorus and from about 10 to about 30 percent alkali metal, with the balance being derived from organic alcohols, all percentages being by weight on a water-free basis. The stabilizer is usually used in the form of an aqueous solution containing from about 20 to about 80 percent by weight of the stabilizer.

The exact structure of the organic phosphate esters of the present invention is not known. However, it is believed that the structure of most of the organic phosphate esters suitable for use as stabilizers for fatty acids is approximately in accordance with the following formulae:

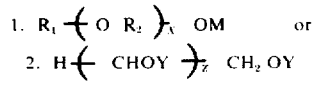

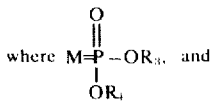

where $M=\overset{O}{\overset{\|}{P}}-OR_3$, and $OR_4$ $R_1$ is hydrogen, $C_1$ to $C_4$ alkyl, phenyl, cresyl, ethyl-phenyl or M. $R_2$ is ethylene, propylene, isopropylene, butylene or butylene isomers. X is a number from 1 to 30, preferably from 1 to 10 and more preferably from 1 to 6. Y is hydrogen or M and at least one Y is M. Z is a number from 1 to 5. $R_3$ and $R_4$ are hydrogen, alkali metal, $H\text{-}(CHOY)_z$ or $R_1\text{-}(OR_2)_x$; at least one $R_3$ or $R_4$ must be an alkali metal.

The alkali metal salts of organic phosphate esters of the present invention, useful as stabilizers of fatty acids, are most clearly described by reference to the materials and reaction for preparing the esters. In general, the stabilizers are prepared by the condensation reaction of a phosphorus compound with particular alcohols, followed by neutralization with an alkali metal base.

The phosphorus must be in the pentavalent state to effect the condensation reaction. Particularly suitable are the use of phosphorus compounds in the pentavalent state. However, phosphorus compounds having phosphorus present in a lower oxidation state may be used if an oxidizing agent is provided during the reaction.

The phosphorus compound is preferably selected from the group consisting of polyphosphoric acid, phosphorus oxychloride, phosphorus pentoxide and inorganic phosphorus salts, such as potassium monohydrogen phosphate and potassium dihydrogen phosphate.

The alcohols useful in effecting the condensation reaction to provide the organic phosphate esters are selected from alcohol ethers and polyols. The alcohol ethers which are useful have the formula:

where $R_1$ is selected from hydrogen, $C_1$ to $C_4$ straight or branched chain alkyl, phenyl, cresyl, ethyl-phenyl and mixtures thereof. $R_2$ is selected from ethylene, propylene, isopropylene, butylene, butylene isomers and mixtures thereof and X is a number from 1 to 30, preferably from 1 to 10 and more preferably from 1 to 6. As used herein, alcohol ethers of the class described are characterized by the term "polyalkylene alcohols". Generally polyalkylene alcohols wherein X is above about 6 do not provide any improved results over polyalkylene alcohols wherein X is 6 or less. For reasons of stability, therefore, it is preferred to use polyalkylene alcohols wherein X is from 1 to 6. Organic phosphate esters prepared from polyalkylene alcohols are generally characterized by formula 1, hereinabove.

Polyols having a carbon chain length of $C_2$ to $C_6$ and mixtures thereof are used to provide organic phosphate esters of the type generally characterized by formula 2, hereinabove. Preferred polyols are ethylene glycol, glycerol, erythritol, xylitol, arabitol, adonitol, sorbitol, mannitol, galactitol, inositol and mixtures thereof.

Other suitable polyols are propylene glycol, pentaerythritol, 1,5-pentanediol, 1,3,-butanediol, 1,4,-butanediol, 2,3,-butanediol, 1,2,4,-butanetriol, 4-methyl-2,4-pentanediol, 1,6,-hexanediol, 2,5,-hexanediol, and mixtures thereof.

In preparing the organic phosphate esters, the alcohol is added to the phosphorus-containing compound and the mixture is thereafter maintained at a temperature of from about 25°C. to about 120°C. and maintained at that temperature for a period of time. Generally a reaction period of from about ½ hour to about 4 hours is sufficient to form the organic phosphate esters. A condenser is used to return condensate to the reaction if the temperature of the reaction is above the boiling point of the alcohol. The phosphorus compound is present at a level sufficient to establish from about 5 to about 15 percent by weight, dry basis, of phosphorus in the final stabilizer product.

The solution is then cooled to a temperature in the range of from about 5° to about 40°C. and an aqueous alkali metal hydroxide is added to the organic phosphate ester at a level sufficient to neutralize the mixture and provide the alkali metal ion at a level sufficient to establish the desired amount of alkali metal ion in the final product. Preferred alkali metal ions for reasons of economy and availability are potassium and sodium. Particularly preferred is potassium.

Particular alcohols which have been found suitable for providing the organic phosphate esters of the present invention are ethylene glycol, propylene glycol, diethylene glycol, triethylene glycol, glycerol, pentaerythritol, 1,5-pentanediol, 1,3,-butanediol, 1,4-butanediol, 2,3,-butanediol, 1,2,4,-butanetriol, 4-methyl-2,4-pentanediol, 1,6-hexanediol, 2,5,-hexanediol, erythritol, xylitol, arabitol, sorbitol, mannitol, galactitol, inositol, di-, tri-, tetra- and penta-ethylene glycol monophenyl ether, di-, tri-, tetra- and penta-ethylene glycol monocresyl ether, di-, tri-, tetra-, and penta-ethylene glycol mono-(ethyl-phenyl) ether, the propylene, isopropylene and butylene equivalents of the aforementioned glycol phenyl ethers, the aforementioned alcohol ethers and mixtures thereof.

Many of the alkali metal salts of organic phosphate esters found suitable as stabilizers for fatty acids in the present invention are characterized in industry as being surfactants. It is a surprising result of the present invention that such surfactant materials can be used as stabilizers to prevent oxidation and darkening of fatty acids. While not wishing to be bound by any theory, it is believed that the phosphate component of the stabilizer is the active agent and that the organic material in combination with the alkali metal act as catalysts and provide a synergistic effect which improves the usefulness of the phosphate as a stabilizer. This improved effect is not provided by adding the separate materials, in the form of alkali metal salts, phosphate salts and alcohol, separately. That is, the improved effect is provided by using alkali metal salts of particular organic phosphate esters and not by the mere presence of the individual compounds alone.

The stabilizers of the present invention are useful for stabilizing both saturated and unsaturated fatty acids having a chain length of $C_6$ to $C_{24}$. The stabilizers are particularly useful to stabilize saturated and unsaturated fatty acids having a chain length of $C_{12}$ to $C_{20}$.

The following examples illustrate various features of the present invention but are intended in no way to limit the scope of the invention which is set forth in the accompanying claims.

EXAMPLE 1

38.7 grams of various alcohols were added to 15.8 grams of polyphosphoric acid in a reaction flask. The alcohol was added under stirring conditions and the mixture was maintained at less than 40°C. under a nitrogen blanket as the alcohol was added. Thereafter, the temperature of the mixture was raised to 105°–110°C. and maintained at that temperature for 2 hours under refluxing conditions. The solution was then cooled to 40°C. and 73.8 grams of 24.4 percent by weight aqueous potassium hydroxide was added to the solution at a rate so that the solution temperature remains in the range of from 25°C. to 40°C. The stabilizer material was then ready to use.

For one example, 8.23 grams of potassium monohydrogen phosphate and 3.31 grams of potassium dihydrogen phosphate was added to 13.26 grams of diethylene glycol and 25.20 grams of distilled water. The mixture was maintained at 90°–100°C. for 2 hours.

0.04 percent by weight of the stabilizer was added to various lots of a mixed fatty acid. The fatty acid contained 1 percent of myristic acid, 49 percent of stearic acid and 50 percent of palmitic acid. Thereafter, the fatty acid with the various stabilizers added thereto was subjected to a high temperature air-oxidation stability test. In this test the fatty acid with the stabilizer present was added to an air-oxidation stability tube at a level of 25.2 grams. The tube was placed in an oil bath for 2 hours at 205°±2°C. Dried air was blown over the fatty acid at a rate of 0.2 standard cubic feet per hour during the 2 hours. After 2 hours, light transmission readings, expressed as percent, are taken at two different wave lengths, namely 440 millimicrons and 550 millimicrons. The higher the percent transmission of light at the two wave lengths, the less oxidation and darkening of the fatty acid has occurred.

Set forth below in Table 1 are the results for various organic phosphate esters.

TABLE I

| Sample No. | Alcohol | Phosphorous Source | Percent Transmission at 440mμ | at 550μ |
|---|---|---|---|---|
| Control | No stabilizer (avg of 3 runs) | | 61 | 89 |
| 1 | Ethylene glycol | Polyphosphoric acid | 77 | 95 |
| 2 | Diethylene glycol | Polyphosphoric acid | 81.5 | 97.5 |
| 3 | Diethylene glycol | $KH_2PO_4$—$K_2HPO_4$ | 77 | 97 |
| 4 | Triethylene glycol | Polyphosphoric acid | 85 | 97.5 |
| 5 | Glycerol | Polyphosphoric acid | 77 | |
| 6 | Sorbitol | Polyphosphoric | 77.3 | 97.3 |

TABLE I-continued

| Sample No. | Alcohol | Phosphorous Source | Percent Transmission at 440mµ | at 550µ |
|---|---|---|---|---|
| | (avg of 3 runs) | acid | | |
| 7 | Diethylene glycol mono-cresyl ether (avg of 2 runs) | Polyphosphoric acid | 86.8 | 98.5 |

In general, a light transmission value at 440 millimicrons in excess of about 70 is desirable for the fatty acids. Preferred is a light transmission value of at least about 75 at 440 millimicrons. Particularly preferred is an absolute transmission value of at least about 80, however an improvement in light transmission value of 10 percent or more over the control is considered acceptable in terms of characterizing the stabilizer material as an effective stabilizer. As can be seen from Table 1, all of the organic phosphate esters described in Table 1 are capable of providing light transmission values in excess of 75 at 440 millimicrons.

Particularly preferred phosphate esters for use as stabilizers for fatty acids in accordance with the present invention are those prepared from polyalkylene glycol mono-cresyl or mono-ethyl phenyl ethers which contain two, three or four alkylene oxide repeating units. Thus, diethylene glycol mono-cresyl and mono-(ethylphenyl) ethers, tri-ethylene glycol mono-cresyl and mono-(ethyl-phenyl) ethers and tetraethylene glycol mono-cresyl and mono-(ethyl-phenyl) ethers are preferred for producing the phosphate esters of the present invention.

A particularly suitable stabilizer for use in the present invention is available under the trade name Triton H-66 from the Rohm and Haas Chemical Company. Other suitable commercially available alkali metal salts of organic phosphate esters are obtainable under the trade names Tanaterge 43 from Tanatex Chemical Company and Atlas G-2200, available from Atlas Chemical Industries. Light transmission values, after the high temperature air-oxidation test described in Example 1 for these three stabilizers are set forth below in Table 2.

action product of an alcohol and a phosphorus compound, said phosphorus being in the pentavalent state during said condensation reaction, said alcohol being selected from the group consisting of poly-alkylene alcohols and hydrocarbyl polyols.

2. A method in accordance with claim 1 wherein said phosphorus compound is selected from the group consisting of polyphosphoric acid, phosphorus oxychloride, phosphorus pentoxide and inorganic phosphorus salts selected from the group consisting of potassium monohydrogen phosphate and potassium dihydrogen phosphate.

3. A method in accordance with claim 1 wherein said polyalkylene alcohol is selected from the group consisting of alcohol ethers which have the formula

where $R_1$ is selected from the group consisting of hydrogen, $C_1$ to $C_4$ straight or branched chain alkyl, phenyl, cresyl, ethyl phenyl and mixtures thereof and $R_2$ is selected from the group consisting of ethylene, propylene, isopropylene, butylene and mixtures thereof and X is a number from 1 to 30.

4. A method in accordance with claim 3 wherein X is a number from 1 to 10.

5. A method in accordance with claim 3 wherein X is a number from 1 to 6.

6. A method in accordance with claim 1 wherein said polyalkylene alcohol is selected from the group consisting of di-, tri-, tetra- and penta-ethylene glycol monophenyl ether, di-, tri-, tetra- and penta-ethylene glycol mono-cresyl ether, di-, tri-, tetra- and penta-ethylene glycol mono-(ethyl-phenyl) ether, the propylene, iso-

TABLE II

| Sample No. | Stabilizer | Level of Use Weight Percent (Dry Basis) | Percent Transmission at 440mµ | at 550mµ |
|---|---|---|---|---|
| Control | No stabilizer | | 59.0 | 91.5 |
| 8 | Triton H-66 | .04 | 81.0 | 94.2 |
| 9 | Tanaterge 43 | .04 | 82.3 | 94.9 |
| 10 | Atlas G-2200 | .04 | 82.3 | 96.0 |

Stabilizers of the present invention are extremely effective and only small amounts are required to effect stabilization of fatty acids. In this connection, the stabilizers are generally added at a level of from about .005 percent to about .05 percent by weight, dry basis, based on the weight of the fatty acids. Higher levels can be used but there is a tendency to exceed the solubility of the stabilizer in the fatty acid and reduce the light transmission value of 550 millimicrons.

What is claimed is:

1. A method for stabilizing fatty acids against oxidation comprising adding to fatty acids having a chain length of $C_6$ to $C_{24}$ an effective amount of a stabilizer, said stabilizer being an alkali metal salt of an organic phosphate ester, said ester being the condensation repropylene and butylene equivalents of the foregoing ethylene glycol phenyl ethers and mixtures thereof.

7. A method in accordance with claim 1 wherein said polyols have a carbon chain length of $C_2$ to $C_6$.

8. A method in accordance with claim 1 wherein said polyols are selected from the group consisting of ethylene glycol, propylene glycol, glycerol, pentaerythritol, 1,5-pentanediol, 1,3-butanediol, 1,4-butanediol, 2,3,-butanediol, 1,2,4,-butanetriol, 4-methyl 2,4 pentanediol, 1,6,-hexanediol, 2,5,-hexanediol, erythritol, xylitol, arabitol, adonitol, sorbitol, mannitol, galactitol, inositol, and mixtures thereof.

9. A method in accordance with claim 1 wherein said alkali metal salt of said condensation reaction product contains from about 5 to about 15 percent by weight, dry basis, of phosphorus and from about 10 to about 30 percent by weight, dry basis, of alkali metal.

10. A method in accordance with claim 1 wherein said alkali metal is selected from the group consisting of potassium and sodium.

11. A method in accordance with claim 1 wherein said alkali metal is potassium.

12. A method in accordance with claim 1 wherein said stabilizer is added to said fatty acid at a level of from about 0.005 to about 0.05 percent by weight dry basis, based on the weight of the fatty acid.

13. Stabilized fatty acids comprising a fatty acid having a chain length of $C_6$ to $C_{24}$ and an effective amount sufficient to inhibit oxidation of a stabilizer, said stabilizer being an alkali metal salt of an organic phosphate ester, said ester being the condensation reaction product of an alcohol and a phosphorus compound, said phosphorus compound being in the pentavalent state during said condensation reaction, said alcohol being selected from the group consisting of poly-alkylene alcohols and hydrocarbyl polyols.

14. Stabilized fatty acids in accordance with claim 13 wherein said phosphorus compound is selected from the group consisting of polyphosphoric acid, phosphorus oxychloride, phosphorus pentoxide and inorganic phosphorus salts selected from the group consisting of potassium monohydrogen phosphate and potassium dihydrogen phosphate.

15. Stabilized fatty acids in accordance with claim 13 wherein said polyalkylene alcohol is selected from the group consisting of alcohol ethers which have the formula

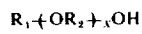

where $R_1$ is selected from the group consisting of hydrogen, $C_1$ to $C_4$ straight or branched chain alkyl, phenyl, cresyl, ethyl-phenyl and mixtures thereof, and $R_2$ is selected from the group consisting of ethylene, propylene, isopropylene, butylene and mixtures thereof and X is a number from 1 to 30.

16. Stabilized fatty acids in accordance with claim 15 wherein X is a number from 1 to 10.

17. Stabilized fatty acids in accordance with claim 15 wherein X is a number from 1 to 6.

18. Stabilized fatty acids in accordance with claim 13 wherein said polyalkylene alcohol is selected from the group consisting of di-, tri-, tetra- and penta-ethylene glycol mono-phenyl ether, di-, tri-, tetra- and penta-ethylene glycol mono-cresyl ether, di-, tri-, tetra-, and penta-ethylene glycol mono-(ethyl-phenyl) ether, the propylene, isopropylene and butylene equivalents of the foregoing ethylene glycol phenyl ethers and mixtures thereof.

19. Stabilized fatty acids in accordance with claim 13 wherein said polyols have a carbon chain length of $C_2$ to $C_8$.

20. Stabilized fatty acids in accordance with claim 13 wherein said polyols are selected from the group consisting of ethylene glycol, propylene glycol, glycerol, pentaerythritol, 1,5-pentanediol, 1,3-butanediol, 1,4-butanediol, 2,3,-butanediol, 1,2,4,-butanetriol, 4-methyl 2,4-pentanediol, 1,6-hexanediol, 2,5,-hexanediol, erythritol, xylitol, arabitol, adonitol, sorbitol, mannitol, galactitol, inositol, and mixtures thereof.

21. Stabilized fatty acids in accordance with claim 13 wherein said alkali metal salt of said condensation reaction product contains from about 5 to about 15 percent by weight, dry basis, of phosphorus and from about 10 to about 30 percent by weight, dry basis, of alkali metal.

22. Stabilized fatty acids in accordance with claim 13 wherein said alkali metal is selected from the group consisting of potassium and sodium.

23. Stabilized fatty acids in accordance with claim 13 wherein said alkali metal is potassium.

24. Stabilized fatty acids in accordance with claim 13 wherein said stabilizer is present at a level of from about 0.005 to about 0.05 percent by weight, dry basis, based on the weight of the fatty acid.

* * * * *